United States Patent [19]

Kobayashi et al.

[11] Patent Number: 5,211,556

[45] Date of Patent: May 18, 1993

[54] ROOT CANAL METER

[75] Inventors: Chihiro Kobayashi, Ichikawa; Kazunari Matoba, Kyoto, both of Japan

[73] Assignee: Kabushiki Kaisha Morita Seisakusho, Kyoto, Japan

[21] Appl. No.: 799,079

[22] Filed: Nov. 27, 1991

[51] Int. Cl.⁵ .................... A61C 3/00; A61C 19/00; A61C 1/00; A61B 5/103

[52] U.S. Cl. ........................ 433/72; 433/27; 128/776

[58] Field of Search ............... 433/27, 72, 75; 128/776, 777

[56] References Cited

U.S. PATENT DOCUMENTS 4,526,179 7/1985 Salesky .................. 128/776
5,049,069 9/1991 Salesky .................. 128/777 X
5,080,586 1/1992 Kawai ................... 128/776 X Primary Examiner—Gene Mancene
Assistant Examiner—Nicholas D. Lucchesi
Attorney, Agent, or Firm—Koda and Androlia

[57] ABSTRACT

A root canal meter is disclosed, wherein measured data are compensated linearly or substantially linearly according to distance between tip of an electrode and apical position and thus compensated data are displayed. According to the invention interrelation between the position of the tip of the measuring electrode and the displayed value becomes clear and also, since the display scarcely varies in the early stage, there is no risk of any sudden change taking place in the vicinity of the apical position, hence the display is easily visible and the meter easy to use.

5 Claims, 2 Drawing Sheets

ROOT CANAL METER

BACKGROUND OF THE INVENTION

1. Field of the Invention

The present invention relates to improvement in root canal meters for diagnosis and treatment in dental practice.

2. Description of Prior Art

As a meter for measuring root canal length electrically there have been known those in which resistance is measured between a measuring electrode and an oral electrode connected to an oral soft tissue (See, for example, Japanese Patent Publication No. 25381 of 1987.) and in which the impedance between both electrodes is measured (See, for example, Japanese Patent Publication No. 2817 of 1987.).

Of the aforementioned patent publication, the former is based on detection of a decrease in the resistance as the tip of the measuring electrode approaches the apical position, while the latter is based on detection of a decrease in the impedance under the same condition. Since the measuring electrode and the oral electrode are deemed to be an equivalent circuit in which a resistor and a capacitor are connected in parallel, the latter, from the viewpoint of measuring principle, is considered better fit for the actual situation.

The rate of change of resistance and capacitor capacity in the aforementioned equivalent circuit when the tip of the measuring electrode is at the dental neck section at the center of the root canal and when it has reached the apical position at the tip of the root canal, is substantially larger in capacitance than resistance, especially the impedance is subject to significantly marked change in the vicinity of the apical position. Hence measured data detected in the form of current or voltage remain low when the measuring electrode is apart from the apical position without any significant increase and starts increasing sharply when the apical position is approached. FIG. 3 shows an example of such a situation, in which the abscissa shows the distance to the apical position and the ordinate the measured data.

Hence, if such measured data are displayed as they are, the displayed value, which remains small with no marked increase when the tip of the measuring electrode is apart from the apical position, suddenly increases when it has come to be approximately 1 mm off the apical position, this making it extremely difficult to use. Such tendency is noticeable to some extent even with that of the resistance detection system but is particularly significant with that of the system of detecting change in impedance.

SUMMARY OF THE INVENTIONS

It is an object of the present invention to solve the aforementioned problem with the prior art. That is, the invention is aimed at providing a root canal meter with which the display changes linearly or substantially linearly according to the distance between the tip of the measuring electrode and the apical position. Another object of the invention is to provide a root canal meter easy to use with the measured value easy to read.

In order to accomplish the above object, the root canal meter of the present invention comprises a data detection means for successively detecting measured data according to the position of the tip of the measuring electrode inserted into the root canal, a data processing means which successively compensates the measured data obtained by the aforementioned data detection means and the compensated data is converted into data which varies linearly or substantially linearly according to the tip of the measuring electrode and the apical position and a display means which displays the compensated data obtained by the aforementioned data processing means.

Treatment by the aforementioned data processing means consists in first having stored in a memory means a table for compensation comprising as compensation values the differences between measured data and the wanted compensated data for individual measured data, reading the proper compensation value from this table and then adding it to the measured data.

It is also possible to have stored in the memory means calculation formula for converting the measured data into the wanted compensated data and use this calculation formula for compensatory calculation of the measured data.

It is also possible to have stored in advance a compensation table in which measured data are given as function of the wanted compensated data so that compensated data can be read direct from the compensation table.

Since the relationship between the distance to the apical position and the measured data shown in FIG. 3 is substantially constant regardless of tooth or patient, hence it is possible to determine the required compensation value for each measured value correspondingly so that the desired compensated data are obtainable and it is thus possible to set in advance compensation table and calculation formula accordingly.

According to the present invention, the measured data varies according to the distance between the tip of the measuring electrode and the apical position linearly or substantially linearly, hence there is no risk of the displayed value rising suddenly in the vicinity of the apical position.

Hence, the interrelation between the position of the tip of the measuring electrode in the form of such as a file and the displayed value becomes clear and at the same time there is precluded the risk of the displayed value varying suddenly due to the measuring principle in which there is scarcely any change in input but a sudden change occurs in the vicinity of the apical position. It becomes easy to do inverse calculation of the approximate distance to the apical position and it is further possible to properly increase the proportion of variation of the displayed value in the vicinity of the apical position. As a result, it becomes possible to provide a root canal meter easy to take reading, capable of giving clinically useful various information and also easy to use.

DETAILED DESCRIPTION OF THE PREFERRED EMBODIMENTS

One illustrated embodiment will be explained below.

Figure 1:
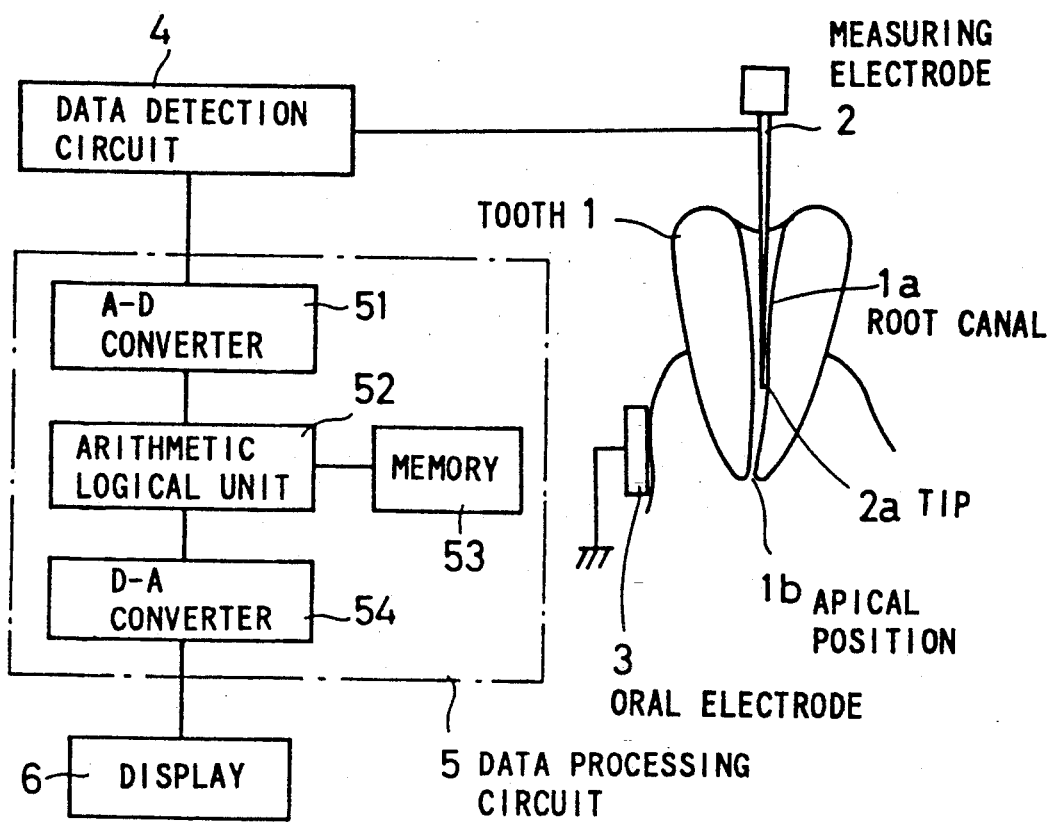
FIG. 1 is a block diagram of one embodiment of the present invention.
Figure 3:
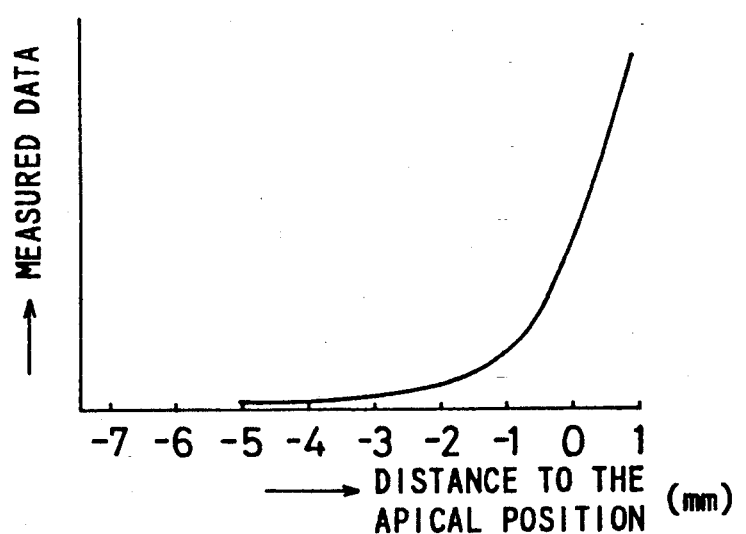
FIG. 3 is an explanatory graph showing the general relationship between the distance to the apical position and the measured data.

In FIG. 1, 1 represents a tooth, 1a and 1b its root canal and apical position, 2 a measuring electrode, 2a its tip, 3 oral electrode, 4 a data detection circuit, 5 a data processing circuit and 6 a display respectively.

The data detection circuit 4 uses a reamer, a file or the like as the measuring electrode 2 and with this inserted into the root canal of the tooth 1, detects the measured data according to the position of its tip successively. Hence, the data detection units of the root canal meter described in the aforementioned patent publications can be utilized as they are. It is, however, also possible to use, for example, the data detection units of the measuring instruments of other systems in which the impedance is detected from the gap between the wave form of the measuring voltage applied between the measuring electrode and the oral electrode and that of the load current flowing between both electrodes as proposed in Japanese Patent Application No. 186330 of 1990 filed on the same day as the present application.

The data processing circuity 5 comprises an A-D converter 51, an arithmetic logical unit 52, a memory 53, a D-A converter 54. The arithmetic logical unit 52 is for successively compensating the measured data obtained in the data detection circuit 4 for outputting the compensated data, and the memory 53 has stored therein various data such as the table for compensation and calculation formula and program for compensatory treating procedure. The A-D converter 51 is for converting analog data into digital data and the D-A converter 54 is for converting digital data into analog data.

the display 6 is for outputting the compensated data from data processing circuit, and may be, besides a common pointer type meter, of such proper meters using light or sound informing means as visual signal light outputting type by the use of an intermittent light emitter and audible signal outputting type by the use of intermittent signal sound generator.

This embodiment is of the composition as described above. Described below is the operation of the present invention using a compensation table for example.

Figure 2:
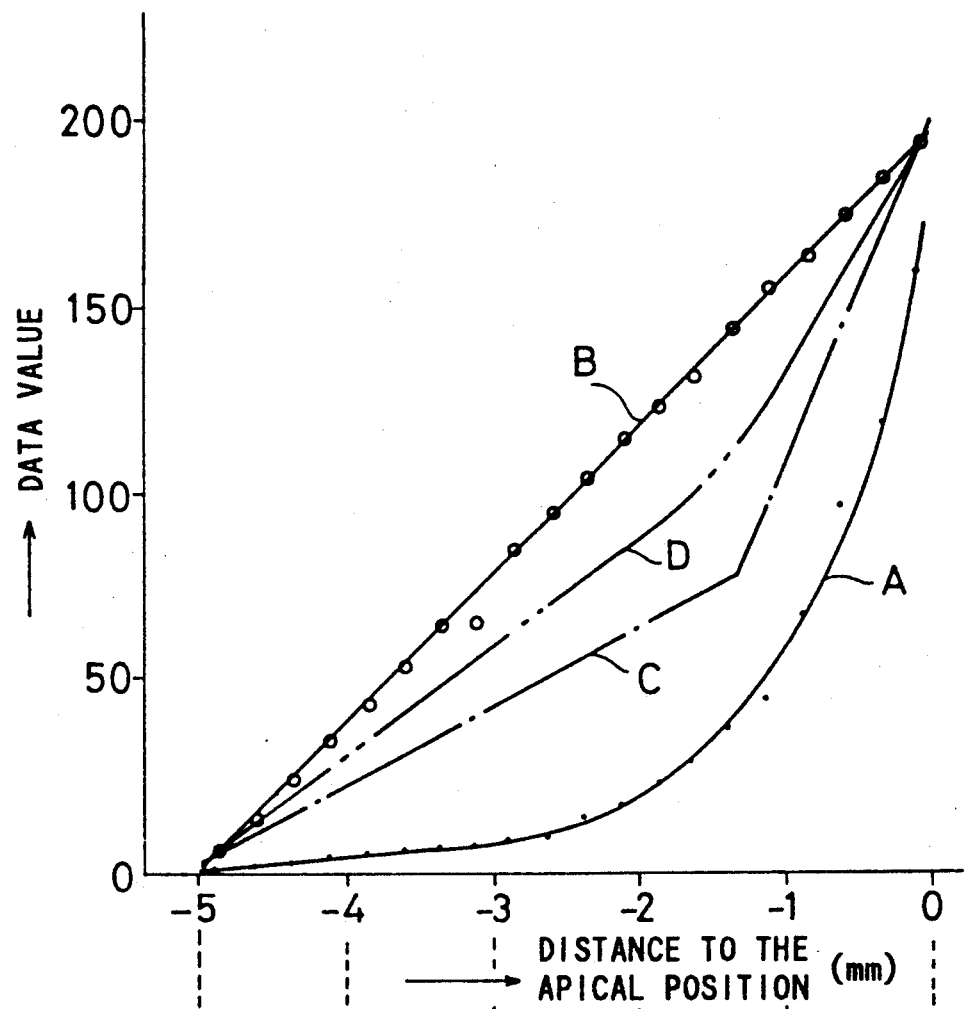
FIG. 2 is an explanatory graph and table showing the relationship among the measured data, the compensation value according to the present invention and the compensated data.

Taken on the abscissa of the graph of FIG. 2 is the distances the tip of 2a of the measuring electrode 2 is to move before it reaches the apical position 1b, while taken on the ordinate thereof are the data values, and the table below the abscissa corresponds to the graph. Given in the upper column of Table 1 are the measured data from the data detection circuit 4 (untreated data corresponding to the curve A of the graph), given in its middle column are the compensation values to be added to the individual measured data and given in the lower column are the compensated values (the final data corresponding to the curve B of the graph). As shown in the figure the compensation values, for instance, 5, 12, 21 . . . 66, 36 are set for the measured data of 1, 2, 3 . . . 120, 160 and these data are stored in advance in the memory 53 as the compensation table. The values of the table are shown by the decimal system but actually they are treated digitally by the use of binary system.

Then, the measuring electrode 2 is inserted into the root canal 1a of the tooth 1 and according to the extent of insertion, the measured data corresponding to the distance between the tip 2a of the measuring electrode 2 and the apical position 1b are outputted from the data detecting circuit 4 and thereupon in the data processing circuit 5 the compensation values of FIG. 2 are added according to the individual measured data respectively and the data thus compensated is displayed on the display 6. Although the measured data increases suddenly as the tip 2a of the measuring electrode 2 approaches the apical position 1b, in this example the compensation value is so selected that the compensated data changes substantially linearly according to the distance to the apical position substantially linearly as shown by the curve B of the figure, and the output signal to the display 6, too, varies substantially linearly.

Hence, if the display 6 is, for example, a pointer type meter, the pointer swings as the measuring electrode 2 is inserted into the root canal 1a roughly in proportion to the extent of insertion, instead of being swung suddenly and extensively as the apical position 1b is approached, and thus a root canal meter easy to use with its display easy to read is obtainable.

The compensated data may, for example, be represented by a straight line the gradient changed half way as seen from curve C which shown by is alternating long and short dash lines. When the plotted result is as indicated by the curve C, the increase proportion of the indicated value is increased as the apical position 1b is approached, this enabling the operator to be warned of the apical position being approached and also enabling enlarged display of movement of the measuring electrode 2 and its position, although the rate of increase is not so sudden as with untreated data. Besides the curve C made up of straight lines different in gradient, similar effect is attainable with the curve D shown by alternate long and two short dashes line made up of a straight line showing the condition when the apical position is away and a curve whose gradient grows steeper as the apical position is approached.

Although the above explanation has been made by the use of the compensation table, compensation is also feasible by the use of a linear expression $y = ax$ with the coefficient 'a' properly selected so that the wanted compensated data are attainable through multiplication of the measured data thereby or another linear expression $y = ax + b$ with constant 'b' to be added as necessary and properly. Although in the embodiment digital treatment is undertaken but compensation is also feasible by analog treatment by successive change of gain, offset et cetera by the use of operational amplifier, multiplier, divider or the like. Such data processing can be done by the use of, for example, an analog multiplier/divider for compression, square root extractor or logarithmic converter.

Instead of adding the compensation value given in the compensation table as mentioned above, or doing calculation by either calculation formula, it is also possible to have the compensation table so prepared that the wanted compensated data is given a function of the measured data so that the individual compensated data can be read directly from the memory.

What is claimed is:

1. A root canal meter, comprising:
   a data detecting means successively detecting measured data corresponding to tip position of a measuring electrode inserted into a root canal,
   a data processing means which successively compensates the measured data obtained by said data detecting means and treats the compensated data to become data varying linearly or substantially linearly according to distance between the tip of the measuring electrode and the apical position of the root canal, and a display means displaying the compensated data obtained by said data processing means.

2. A root canal meter according to claim 1, wherein said root canal meter has memory means and a compensation table for converting the measured data into the compensated data in its memory means and said root canal meter is so arranged that a compensation value of said compensation table is added to the measured data for compensation.

3. A root canal meter according to claim 1, wherein a calculating formula for converting the measured data into the compensated data is stored in said memory means and said calculating formula is used for compensation of the measured data.

4. A root canal meter according to claim 1, wherein the measured data and the compensated data are tabulated as a function of each other as another compensation table from which the compensated data can be read directly.

5. A root canal meter according to claim 1, wherein an analog multiplier/divider, square root extractor or logarithmic converter is used as a data processing means for converting the measured data into the compensated data.

* * * * *